(12) United States Patent
Blanton et al.

(10) Patent No.: US 8,338,514 B2
(45) Date of Patent: Dec. 25, 2012

(54) POLYOLEFIN ANTIMICROBIAL COMPOSITIONS AND MELT-PROCESSING METHODS

(75) Inventors: Thomas N. Blanton, Rochester, NY (US); David W. Sandford, Rochester, NY (US); Kevin L. Bishop, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 856 days.

(21) Appl. No.: 12/339,566

(22) Filed: Dec. 19, 2008

(65) Prior Publication Data

US 2010/0160486 A1 Jun. 24, 2010

(51) Int. Cl.
*C08K 5/00* (2006.01)

(52) U.S. Cl. .......... 524/236; 524/392; 524/403

(58) Field of Classification Search .......... 524/392, 524/403, 236
See application file for complete search history.

(56) References Cited

U.S. PATENT DOCUMENTS

| | | | |
|---|---|---|---|
| 4,938,955 A | 7/1990 | Niira et al. | |
| 6,187,456 B1 | 2/2001 | Lever | |
| 6,468,521 B1 | 10/2002 | Pedersen et al. | |
| 6,585,989 B2 | 7/2003 | Herbst et al. | |
| 7,041,723 B2 | 5/2006 | Kimura | |
| 2003/0125413 A1* | 7/2003 | Herbst et al. | 523/122 |
| 2008/0181969 A1 | 7/2008 | Blanton et al. | |
| 2008/0242794 A1 | 10/2008 | Sandford et al. | |

FOREIGN PATENT DOCUMENTS

| | | |
|---|---|---|
| JP | 62-270642 | 11/1987 |
| JP | 04/114038 | 4/1992 |
| WO | 2004/033545 | 4/2004 |
| WO | 2007/042416 | 4/2007 |
| WO | 2008/046746 | 4/2008 |

* cited by examiner

*Primary Examiner* — Peter D Mulcahy
(74) *Attorney, Agent, or Firm* — J. Lanny Tucker

(57) ABSTRACT

A melt-processed polyolefin composition or composite includes a polyolefin compounded with a hindered amine light stabilizer, an organodisulfide antioxidant, and silver sulfate as an antimicrobial agent. A process of preparing such a composite includes compounding all of the compounds in various orders as long as the silver sulfate is added after the hindered amine light stabilizer is added to the polymer.

22 Claims, No Drawings

POLYOLEFIN ANTIMICROBIAL COMPOSITIONS AND MELT-PROCESSING METHODS

FIELD OF THE INVENTION

The present invention relates to improvements in color stability upon exposure to light of melt-processed thermoplastic polymer composites and compositions, and plastic objects made therefrom, within which a silver-based antimicrobial agent has been introduced. More particularly, the invention is directed towards use of a combination of organodisulfides and hindered amine light stabilizers in such polymer composites, and improved methods of compounding the compositions.

BACKGROUND OF THE INVENTION

Widespread attention has been focused in recent years on the consequences of bacterial contamination contracted by food consumption or contact with common surfaces and objects. Allergic reactions to molds and yeasts are also a major concern. Respiratory infections due to viruses such as SARS (severe acute respiratory syndrome) coronavirus, and the H5N1 virus and mutations thereof, now commonly referred to as the avian flu or bird flu, have become major public health issues. In addition, significant fear has arisen in regard to the development antibiotic-resistant strains of bacteria, such as methicillin-resistant *Staphylococcus aureus* (MRSA) and vancomycin-resistant *Enterococcus* (VRE). In response to these concerns, manufacturers have begun incorporating antimicrobial agents into materials used to produce objects for commercial, institutional and residential use.

The antimicrobial properties of silver have been known for several thousand years. The general pharmacological properties of silver are summarized in "Heavy Metals" and "Antiseptics and Disinfectants: Fungicides; Ectoparasiticides"—by Stewart C. Harvey in *The Pharmacological Basis of Therapeutics*, Fifth Edition, by Louis S. Goodman and Alfred Gilman (editors), published by MacMillan Publishing Company, NY, 1975. It is now understood that the affinity of silver ion for biologically important moieties such as sulfhydryl, amino, imidazole, carboxyl and phosphate groups are primarily responsible for its antimicrobial activity. The attachment of silver ions to one of these reactive groups on a protein results in the precipitation and denaturation of the protein. The extent of the reaction is related to the concentration of silver ions. The diffusion of silver ion into mammalian tissues is self-regulated by its intrinsic preference for binding to proteins through the various biologically important moieties on the proteins, as well as precipitation by the chloride ions in the environment. Thus, the very affinity of silver ion to a large number of biologically important chemical moieties (an affinity which is responsible for its action as a germicidal/biocidal/viricidal/fungicidal/bacteriocidal agent) is also responsible for limiting its systemic action—silver is not easily absorbed by the body. This is a primary reason for the tremendous interest in the use of silver containing species as an antimicrobial i.e. an agent capable of destroying or inhibiting the growth of microorganisms, including bacteria, yeast, fungi and algae, as well as viruses.

In addition to the affinity of silver ions for biologically relevant species, which leads to the denaturation and precipitation of proteins, some silver compounds, those having low ionization or dissolution ability, also function effectively as antiseptics. Distilled water in contact with metallic silver becomes antibacterial even though the dissolved concentration of silver ions is less than 100 ppb. There are numerous mechanistic pathways by which this oligodynamic effect is manifested i.e. by which silver ion interferes with the basic metabolic activities of bacteria at the cellular level, thus leading to a bacteriocidal or bacteriostatic effect.

While it is well known that silver-based agents provide excellent antimicrobial properties, aesthetic problems due to discoloration is frequently a concern. This is believed to be due to several root causes, including the inherent thermal and photo-instability of silver ions, along with other mechanisms. A wide range of silver salts are known to be thermally and photolytically unstable, discoloring to form brown, gray or black products. Silver ion may be formally reduced to its metallic state, assuming various physical forms and shapes (particles and filaments), often appearing brown, gray or black in color. Reduced forms of silver in the form particles of sizes on the order of the wavelength of visible light may also appear to be pink, orange, yellow, or beige due to light scattering effects. Alternatively, silver ion may be formally oxidized to silver peroxide, a gray-black material. In addition, silver ion may simply complex with environmental agents (for example, polymer additives, catalyst residues, impurities, and surface coatings) to form colored species without undergoing a formal redox process. Silver ion may attach to various groups on proteins present in human skin, resulting in the potentially permanent dark stain condition known as argyria. While pure silver sulfate is colorless, it has been observed to decompose upon exposure to light to a violet color. While the formation of colored species of silver or of other additives that impart discoloration to a plastic composition or fiber may be undesirable in itself, given that colorants are often intentionally added to produce a specific desired coloration, it is of greater practical importance that any discoloration imparted by an additive be stable over the useful lifetime of the composition, fiber or object made therefrom.

In any given practical situation, a number of mechanisms or root causes may be at work in generating silver-based discoloration, complicating the task of providing a solution to the problem. For example, U.S. Pat. Nos. 6,468,521 and 6,726,791, disclose the development of a stabilized wound dressing having antibacterial, antiviral and/or antifungal activity characterized in that it comprises silver that is complexed with a specific amine and is associated with one or more hydrophilic polymers, such that it is stable during radiation sterilization and retains the activity without giving rise to darkening or discoloration of the dressing during storage. Registered as CONTREET®, the dressing product comprises a silver compound complexed specifically with either ethylamine or tri-hydroxymethyl-aminomethane. These specific silver compounds, when used in conjunction with the specific polymer binder carboxymethylcellulose or porcine collagen, are said to have improved resistance to discoloration when exposed to heat, light or radiation sterilization and contact with skin or tissue.

The point in time when discoloration of a composition associated with a silver-based additive appears can range from early in the manufacturing process to late in a finished article's useful life. For example, thermal instability can set in shortly after introduction of the silver-based additive into a high temperature melt-processed polymer, or much later during long-term storage of the material or finished article at lower (e.g. ambient) temperatures, sometimes referred to as long-term heat stability. Likewise, photo-instability can result from short-term exposure to high-energy radiation processing or radiation sterilization, or later from long-term exposure of the material or finished article to ambient light (for example, requiring ultraviolet (UV) stabilization). In addition, polymeric materials are well known to inherently discolor to some degree either during high temperature melt processing, or later due to aging in the presence of light, oxygen and heat. Thermoplastic polymers such as polyolefins are typically processed at temperatures between about 130-300° C. and will degrade under these conditions by an oxidative chain reaction process that is initiated by free-radical formation. Free radicals (R*) formed either along the polymer backbone or at terminal positions will react quickly with oxygen ($O_2$) to form peroxy radicals (ROO*), which in turn can react with the polymer to form hydroperoxides (ROOH) and another free radical (R*). The hydroperoxide can then split into two new free radicals, (RO*) and (*OH), which will continue to propagate the reaction to other polymer chains. It is known in the art that antioxidants and light stabilizers can prevent or at least reduce the effects of these oxidative chain reactions. Antioxidant stabilizers are typically classified as (1) free-radical scavengers or primary antioxidants, and (2) hydroperoxide decomposers or secondary antioxidants. Hindered amine light stabilizers are believed to act in part as free-radical and peroxy radical scavengers through the formation of nitroxyl radicals.

Primary antioxidants are added to polymers mainly to improve long-term heat stability of the final fabricated article. Primary antioxidants are often called free radical scavengers because they are capable of reacting quickly with peroxy or other available free radicals to yield an inert or much less reactive free radical species, thus halting or slowing down the oxidative chain reaction process that leads to degradation. Primary antioxidants typically include, for instance, sterically hindered phenols, secondary aromatic amines, hydroquinones, p-phenylenediamines, quinolines, hydroxytriazines or ascorbic acid (vitamin C). Although aromatic amines are the strongest primary antioxidant, they are highly staining and seldom used in thermoplastics.

Secondary antioxidants are added to polymers mainly to provide needed short-term stability in melt flow and color during high temperature melt processing of the plastic material. They are believed to function by reacting with hydroperoxides to yield stable products that are less likely to fragment into radical species. Secondary antioxidants can usually be classified chemically as either a phosphorous-containing or a sulfur-containing compound. Phosphites such as triesters of phosphoric acid ($P(OR')_3$) are believed to react with hydroperoxides (ROOH) to form phosphates ($OP(OR')_3$) and alcohols (ROH). Elemental sulfur compounds and diaryl disulfides are reported to decompose hydroperoxides by generating sulfur dioxide. Thioethers ($R_1SR_2$) are believed to react with hydroperoxides (ROOH) to yield sulfoxides ($R_1SOR_2$) and alcohols (ROH). Sulfoxides may in turn destroy several equivalents of hydroperoxide through the intermediate formation of sulfenic acids and sulfur dioxide.

A third group of antioxidant stabilizers is commonly referred to as synergists. These materials may not be effective stabilizers when used alone, but when used in combination with another antioxidant a cooperative action results wherein the total effect is greater than the sum of the individual effects. Carbon black acts synergistically when combined with elemental sulfur, thiols or disulfides, whereas these materials are largely ineffective when used alone under the same conditions. Homosynergism is used to describe two stabilizers of unequal activity that work by the same mechanism. For example, two radical scavenging primary antioxidants might function synergistically if one were to transfer a hydrogen atom to the radical formed by the other, thus regenerating the latter stabilizer and extending its effectiveness. Alternatively, heterosynergism might result between a free radical scavenger and a nonradical hydroperoxide decomposer that act on different portions of the oxidative chain reaction process that leads to decomposition. Ultraviolet absorbers or metal deactivators in combination with radical scavengers have also been report to be heterosynergists. Some common thiosynergists include the esters of β-thiodipropionic acid, for example the lauryl, stearyl, myristyl or tridecyl esters. A widely used antioxidant package for polyolefins is the primary antioxidant 2,6-di-tert-butyl-4-methylphenol (BHT) with the thiosynergist dilauryl thiodipropionate (DLTDP).

A rapidly emerging application for silver based antimicrobial agents is inclusion in polymers used in plastics and synthetic fibers. A variety of methods is known in the art to render antimicrobial properties to a target fiber. The approach of embedding inorganic antimicrobial agents, such as zeolite, into low melting components of a conjugated fiber is described in U.S. Pat. Nos. 4,525,410 and 5,064,599. In another approach, the antimicrobial agent may be delivered during the process of making a synthetic fibers such as those described in U.S. Pat. Nos. 5,180,402, 5,880,044, and 5,888,526, or via a melt extrusion process as described in U.S. Pat. Nos. 6,479,144 and 6,585,843. Alternatively, deposition of antimicrobial metals or metal-containing compounds onto a resin film or target fiber has also been described in U.S. Pat. Nos. 6,274,519 and 6,436,420. Still, the formation of colored species of silver that impart discoloration to a plastic composition or fiber is clearly undesirable from both an aesthetic and a practical materials performance perspective.

In addition to the color instabilities inherent to silver and to polymeric materials themselves, silver ion imbedded in polymer composites may react with polymer decomposition products (for example, free radicals, peroxides, hydroperoxides, alcohols, hydrogen atoms and water), modifiers (for example, chlorinated flame retardants), stabilizers and residual addenda (for example, titanium tetrachloride, titanium trichloride, and trialkylaluminum compounds from Ziegler-Natta catalysts) to form potentially unstable colored byproducts. This greater complexity of potential chemical interactions further challenges the modern worker in designing an effective stabilizer package for polymers containing silver species.

A number of approaches have been taken in the past to improve the light stability of melt-processed polymer composites containing a silver-based antimicrobial agent. Niira et al. in U.S. Pat. No. 4,938,955 disclose melt-processed antimicrobial resin compositions comprising a silver containing zeolite and a single stabilizer (discoloration inhibiting agent) selected from the group consisting of a hindered amine (CHIMASSORB 944LD or TINUVIN 622LD), a benzotriazole, a hydrazine, or a hindered phenol. Reduction in long-term discoloration from exposure to 60 days of sunlight in the air is reported. Ohsumi et al. in U.S. Pat. No. 5,405,644 disclose a fiber treatment process in which the addition of a benzotriazole, such as methylbenzotriazole, to treatment solutions subsequently inhibits discoloration in fibers comprising a silver containing tetravalent-metal phosphate antimicrobial agent following one day exposure to outdoor sunlight. Herbst in U.S. Pat. No. 6,585,989 adds a silver containing zeolite to a chlorinated bisphenol ether antimicrobial agent (TRICLOSAN® 2,4,4'-trichloro-2'-hydroxydiphenyl ether) in polyethylene and polypropylene to yield improved UV stabilization (reduced yellowing) in accelerated weathering tests. Kimura in U.S. Pat. No. 7,041,723 discloses that for polyolefins containing an antimicrobial combination consisting of (a) a silver containing zeolite and either (b) a silver ion-containing phosphate or (c) a soluble silver ion-containing glass powder, some drawbacks of each antimicrobial agent are mitigated, including the reduction of discoloration from UV light exposure in accelerated weathering tests.

Copending and commonly assigned U.S. Ser. No. 11/669,830 (filed Jan. 31, 2007 by Blanton, Dontula, Jagannathan, Bishop, Sandford, and Barnes) describes thermoplastic compositions comprising polyolefins, primary antioxidants, secondary antioxidants, and silver salts. Herbst in WO 2007/042416 describes antimicrobial garments and footwear comprising a phenolic antibacterial agent, specific antifungal agents, and optionally a silver ion releasing agent, in polyester or polyvinylchloride resins. Schneider et al. in WO 2008/046746 describe durable acaricidal resin formulations comprising a dust mite killing agent (preferably thiabendazol) and, optionally, an antimicrobial agent consisting of a phenolic compound and/or silver metal or a silver complex or silver salt, incorporated into the bulk of a polymer.

We have discovered that polyolefin masterbatch composites comprising silver sulfate and large amounts (25 weight %) of polymeric hindered amine light stabilizers exhibit very poor light stability. Thus, there is a need to provide compositions and articles comprising thermoplastic polyolefins, silver sulfate and a hindered amine light stabilizer with improved light stability.

SUMMARY OF THE INVENTION

This invention provides a melt-processed composition comprising a polyolefin having dispersed therein at least 0.01 weight % of silver sulfate, at least 0.5 weight % of a hindered amine light stabilizer, and at least 0.001 weight % of an organo-disulfide.

This invention also provides a melt-processed composition that is a masterbatch composition comprising at least 0.1 weight % silver sulfate, at least 5 weight % of a hindered amine light stabilizer, and at least 0.01% of an organo-disulfide, and that has a b*IF value greater than zero. The b*IF value is defined below with the Examples.

Further, this invention provides melt-processed film, fiber, or article comprising a polyolefin having dispersed therein at least 0.01 weight % of silver sulfate, at least 0.1 weight % of a hindered amine light stabilizer, and at least 0.001 weight % of an organo-disulfide.

Also, this invention provides a melt-processing method of preparing a polyolefin composition with antimicrobial properties, comprising:

A) blending a polyolefin, hindered amine light stabilizer, and organo-disulfide, in any order, to provide a polyolefin composite, and B) subsequently, adding silver sulfate to the polyolefin composite.

In addition, a process of forming a polymer composite comprising a polyolefin, a hindered amine light stabilizer, an organo-disulfide additive, and silver sulfate, wherein the composite has a b*IF value greater than zero, comprises:

heating the polyolefin at least to melting point;
obtaining the hindered amine light stabilizer,
obtaining the silver sulfate antimicrobial agent,
obtaining the organo-disulfide additive, and
carrying out one of the following options a) through c) to form the polymer composite:

a) compounding the heated polyolefin with the hindered amine light stabilizer and the organo-disulfide additive, then adding the silver sulfate antimicrobial agent, b) mixing the silver sulfate antimicrobial with the organo-disulfide additive, then compounding the resulting mixture with the heated polyolefin and the hindered amine light stabilizer, and c) compounding the heated polyolefin and hindered amine light stabilizer with the silver sulfate antimicrobial agent, then adding the organo-disulfide additive.

The instant invention is directed primarily at improving light stability in melt-processed thermoplastic polyolefin, silver sulfate-based compositions containing hindered amine light stabilizers. Thus, the present invention is a means for minimizing the change in coloration due to light exposure of the compositions or resulting articles. We have unexpectedly found that the use of an organo-disulfide in combination with silver sulfate in such compositions reduces coloration change upon light exposure.

In addition, we found advantages for some embodiments of the method of compounding. For example, if the silver sulfate is compounded into the composite after the hindered amine light stabilizer and polyolefin have been mixed, then color change may be reduced even further.

DETAILED DESCRIPTION OF THE INVENTION

The melt-processed compositions, composites, masterbatches, articles, films, and fibers of this invention have a b*IF value greater than zero, or typically greater than or equal to 0.35. The b*IF value is defined below in the Examples.

The present invention provides improvements in color stability upon exposure to light of melt-processed polyolefins and plastic objects made there of, within which silver sulfate antimicrobial agent has been introduced. Polyolefins suitable to the invention include those melt-processed between about 130-300° C. Examples of such polymeric materials include:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked, known as PEX), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

2. Mixtures of the polymers mentioned above, for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinyl cyclohexane copolymers, ethylene/cycloolefin copolymers (for example, ethylene/norbornene like COC), ethylene/1-olefins copolymers, where the 1-olefin is generated in-situ; propylene/butadiene copolymers, isobutylene/isoprene copolymers, ethylene/vinyl cyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random poly-alkylene/carbon monoxide copolymers and mixtures thereof with other polymers.

Homopolymers and copolymers described above may have any stereostructure, including syndiotactic, isotactic, hemi-isotactic or atactic. Stereoblock polymers are also included. The polymers may be amorphous, crystalline, or semicrystalline and possess a range of melt index of from about 0.3 to about 99.

Polyolefins particularly include polyethylene and polypropylene and can be prepared by different known methods, such as the following, methods: a) radical polymerization (normally under high pressure and at elevated temperature); b) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, the metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

The silver-based antimicrobial agent for incorporation into polyolefins is silver sulfate. Silver sulfate employed may be obtained from various commercially available sources (such as Cascade Chemicals, Riverside Chemical, and Aldrich Chemical Co.), and may be produced by conventional aqueous precipitation methods. The reaction of equimolar amounts of aqueous solutions of silver nitrate and sulfuric acid to form silver sulfate was described by Th. W. Richards and G. Jones, Z. anorg. Allg. Chem. 55, 72 (1907). A similar precipitation process using sodium sulfate as the source of sulfate ion was reported by O. Honigschmid and R. Sachtleben, Z. anorg. Allg. Chem. 195, 207 (1931). An alternate method employing the immersion of silver metal in a sulfuric acid solution was also reported by O. Honigschmid and R. Sachtleben (loc. cit.). Precipitation of finely divided silver sulfate from an aqueous solution via the addition of alcohol was later reported by H. Hahn and E. Gilbert, Z. anorg. Allg. Chem. 258, 91 (1949).

Silver sulfate also may be obtained by a process wherein an aqueous solution of a soluble silver salt and an aqueous solution of a source of inorganic sulfate ion are added together under turbulent mixing conditions in a precipitation reactor. Soluble silver salts that may be employed in the process include silver nitrate, acetate, propionate, chlorate, perchlorate, fluoride, lactate, etc. Inorganic sulfate ion sources include sulfuric acid, ammonium sulfate, alkali metal (lithium, sodium, potassium, rubidium, cesium) sulfate, and alkaline earth metal (such as magnesium) sulfate, and transition metal (such as zinc, cadmium, zirconium, yttrium, copper, nickel, and iron) sulfate. In a specific embodiment, the soluble silver salt employed is silver nitrate and the source of inorganic sulfate ion is ammonium sulfate or sulfuric acid.

Once formed in an aqueous precipitation process, the resulting silver sulfate particles may be washed, dried and collected as a white free-flowing powder. In terms of particle size metrics, the precipitation process preferably results in producing both a small primary crystallite size and a small grain size, along with a narrow grain size distribution. While not limited in the present invention, average particle sizes of less than 100 μm and even less than 50 μm may be desired for particular product applications.

The useful organo-disulfides may be classified as diaryl, dialkyl or mixed alkylaryl disulfides. Specific useful embodiments include diphenyl disulfide and dioctadecyl disulfide (also named distearyl disulfide).

Sterically hindered amine light stabilizers (HALS) useful in the present invention can be derivatives of 2,2,6,6-tetramethyl piperidine and are well known as efficient polymer stabilizers against light-induced degradation. HALS may be classified in a number of ways, such as 1) physical form (powder or liquid), 2) molecular weight (low or high), and 3) substitution at the piperidinyl nitrogen. HALS that are unsubstituted at the piperidinyl nitrogen atom are referred to as N—H type, those methyl substituted are referred to as N—Me type, those alkoxy substituted are referred to as N—OR type, and those alkyl substituted are generally referred to as N—R type.

Low-molecular weight HALS are generally more effective than high-molecular weight HALS on a per weight basis and are commonly referred to as HALS-I materials. Low-molecular weight HALS can be monomeric in structure and contain one or more of the substituted or unsubstituted 2,2,6,6-tetramethyl piperidinyl moieties. A non-limiting list of monomeric HALS includes:
4-hydroxy-2,2,6,6-tetramethylpiperidine,
1-allyl-4-hydroxy-2,2,6,6-tetramethylpiperidine,
1-benzyl-4-hydroxy-2,2,6,6-tetramethylpiperidine,
bis(2,2,6,6-tetramethyl-4-piperidyl)sebacate,
bis(2,2,6,6-tetramethyl-4-piperidyl)succinate,
bis(1,2,2,6,6-pentamethyl-4-piperidyl)sebacate,
bis(1-octyloxy-2,2,6,6-tetramethyl-4-piperidyl)sebacate,
bis(1,2,2,6,6-pentamethyl-4-piperidyl)n-butyl-3,5-di-tert-butyl-4-hydroxybenzylmalonate,
tris(2,2,6,6-tetramethyl-4-piperidyl)nitrilotriacetate,
tetrakis(2,2,6,6-tetramethyl-4-piperidyl)-1,2,3,4-butane-tetracarboxylate,
1,1'-(1,2-ethanediyl)-bis(3,3,5,5-tetramethylpiperazinone),
4-benzoyl-2,2,6,6-tetramethylpiperidine,
4-stearyloxy-2,2,6,6-tetramethylpiperidine,
bis(1,2,2,6,6-pentamethylpiperidyl)-2-n-butyl-2-(2-hydroxy-3,5-di-tert-butylbenzyl)malonate,
3-n-octyl-7,7,9,9-tetramethyl-1,3,8-triazaspiro[4.5]decan-2,4-dione,
bis(1-octyloxy-2,2,6,6-etramethylpiperidyl)sebacate,
bis(1-octyloxy-2,2,6,6-tetramethyl-piperidyl)succinate,
the condensate of 2-chloro-4,6-bis(4-n-butylamino-2,2,6,6-tetramethylpiperidyl)-1,3,5-triazine and 1,2-bis(3-aminopropylamino)ethane,
the condensate of 2-chloro-4,6-di-(4-n-butylamino-1,2,2,6,6-pentamethylpiperidyl)-1,3,5-triazine and 1,2-bis-(3-aminopropylamino)ethane,
8-acetyl-3-dodecyl-7,7,9,9-tetramethyl-1,3,8-triazaspiro [4.5]decane-2,4-dione,
3-dodecyl-1-(2,2,6,6-tetramethyl4-piperidyl)pyrrolidin-2,5-dione,
3-dodecyl-1-(1,2,2,6,6-pentamethyl-4-piperidyl)pyrrolidine-2,5-dione,
a mixture of 4-hexadecyloxy- and 4-stearyloxy-2,2,6,6-tetramethylpiperidine, N-(2,2,6,6-tetramethyl-4-piperidyl)-n-dodecylsuccinimide,
N-(1,2,2,6,6-pentamethyl-4-piperidyl)-n-dodecylsuccinimide,
2-undecyl-7,7,9,9-tetramethyl-1-oxa-3,8-diaza-4-oxo-spiro [4,5]decane
1,1-bis(1,2,2,6,6-pentamethyl-4-piperidyloxycarbonyl)-2-(4-methoxyphenyl)ethane,
N,N'-bis-formyl-N,N'-bis(2,2,6,6-tetramethyl-4-piperidyl) hexamethylenediamine, and
a diester of 4-methoxy-methylene-malonic acid with 1,2,2,6, 6-pentamethyl-4-hydroxypiperidine.

A low-molecular weight HALS may also be one of the monomeric compounds described in GB-A-2,301,106 among components I-a), I-b), I-c), I-d), I-e), I-f), I-g), I-h), I-i), I-j), I-k) or I-l), in particular the light stabilizers 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on pages 68 to 73 of this publication.

A low-molecular weight HALS may also be one of the monomeric compounds described in EP Publication 782,994, for example among compounds as described in claim 10 or 38 or in Examples 1-12 or D-1 to D-5 therein.

A low-molecular weight HALS may also be a monomeric compound substituted on the piperidinyl N-atom by a hydroxy-substituted alkoxy group, for example compounds such as the following:
1-(2-hydroxy-2-methylpropoxy)-4-octadecanoyloxy-2,2,6, 6-tetramethylpiperidine,
1-(2-hydroxy-2-methylpropoxy)-4-hexadecanoyloxy-2,2,6, 6-tetramethylpiperidine,
the reaction product of 1-oxyl-4-hydroxy-2,2,6,6-tetramethylpiperidine with a carbon radical from t-amylalcohol,
1-(2-hydroxy-2-methylpropoxy)-4-hydroxy-2,2,6,6-tetramethylpiperidine,
1-(2-hydroxy-2-methylpropoxy)-4-oxo-2,2,6,6-tetramethylpiperidine,
bis(1-(2-hydroxy-2-methylpropoxy)-2,2,6,6-tetramethylpiperidin-4-yl)sebacate,
bis(1-(2-hydroxy-2-methylpropoxy)-2,2,6,6-tetramethylpiperidin-4-yl)adipate,
bis(1-(2-hydroxy-2-methylpropoxy)-2,2,6,6-tetramethylpiperidin-4-yl)succinate,
bis(1-(2-hydroxy-2-methylpropoxy)-2,2,6,6-tetramethylpiperidin-4-yl)glutarate, and
2,4-bis{N-[1-(2-hydroxy-2-methylpropoxy)-2,2,6,6-tetramethylpiperidin-4-yl]-N-butylamino}-6-(2-hydroxyethylamino)-s-triazine.

High-molecular weight HALS are useful in that they are less volatile, less migrating, less extractable by solvents, more imparting of mechanical strength and more durable in applications requiring a long use of the plastic material. High-molecular weight HALS can be polymeric in nature and as such contain at least two polymeric repeat units, wherein each repeat unit contains one or more of the substituted or unsubstituted 2,2,6,6-tetramethyl piperidinyl moieties. Polymeric HALS for use in the invention that incorporate the 2,2,6,6-tetramethyl piperidinyl moiety directly into the polymer backbone are referred to as polymeric HALS-II, and include, for example, poly-(N-β-hydroxyethyl-2,2,6,6-tetramethyl-4-hydroxypiperidyl succinate) (commercially available as TINUVIN® 622 (CAS Reg. No. [65447-77-0]). Polymeric HALS for use in the invention that incorporate the substituted or unsubstituted 2,2,6,6-tetramethyl piperidinyl moiety as pendant substituent groups attached to a polymer backbone are referred to as polymeric HALS-III materials, and include, for example, the following:

linear or cyclic condensates of N,N'-bis(2,2,6,6-tetramethyl-4-piperidyl)hexamethylenediamine and 4-tert-octylamino-2,6-dichloro-1,3,5-triazine (CAS Reg. No. [71878-19-8]),
linear or cyclic condensates of N,N'-bis-(2,2,6,6-tetramethyl-4-piperidyl)-hexamethylenediamine and 4-morpholino-2,6-dichloro-1,3,5-triazine,
a condensation product of N,N'-bis(2,2,6,6-tetramethyl-4-piperidyl)hexamethylenediamine and 4-cyclohexylamino-2, 6-dichloro-1,3,5-triazine,
a condensation product of 1,2-bis(3-aminopropylamino) ethane and 2,4,6-trichloro-1,3,5-triazine as well as 4-butylamino-2,2,6,6-tetramethylpiperidine (CAS Reg. No. [136504-96-6]),
a condensation product of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]),
a reaction product of 7,7,9,9-tetramethyl-2-cycloundecyl-1-oxa-3,8-diaza-4-oxospiro[4,5]decane and epichlorohydrin,
poly[methylpropyl-3-oxy-4-(2,2,6,6-tetramethyl-4-piperidyl)]siloxane, and
reaction product of maleic acid anhydride-α-olefin-copolymer with 2,2,6,6-tetramethyl-4-aminopiperidine or 1,2, 2,6,6-pentamethyl-4-aminopiperidine.

A high-molecular weight HALS may also be one of the polymeric compounds described in GB-A-2,301,106 among components I-a), I-b), I-c), I-d), I-e), I-f), I-g), I-h), I-i), I-j), I-k) or I-l), in particular the light stabilizers 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on pages 68 to 73 of this publication.

A high-molecular weight HALS may also be one of the polymeric compounds described in EP 782994, for example among compounds as described in claim 10 or 38 or in Examples 1-12 or D-1 to D-5 therein.

Thus, the melt-processed composition can include a polymeric sterically hindered amine light stabilizer.

In some embodiments of this invention, the melt-processed composition comprises a polymeric hindered amine light stabilizer that is selected from the group consisting of:
a) 1,3-propanediamine,N,N'''-1,2-ethanediylbis-, polymer with 2,4,6-trichloro-1,3,5-triazine, reaction products with N-butyl-2,2,6,6-tetramethyl-4-piperidinamine (commercially available as UVASORB® HA88 FD),
b) poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]] (commercially available as CHIMASSORB® 944), and
c) 1,6-hexanediamine, N1,N6-bis(2,2,6,6-tetramethyl-4-piperidinyl)-, polymer with 2,4,6-trichloro-1,3,5 triazine, reaction products with, N-butyl-1-butanamine and N-butyl-2,2,6,6-tetramethyl-4-piperidinamine (commercially available as CHIMASSORB® 2020); and
an organo-disulfide that is octadecyl disulfide or diphenyl disulfide.

The melt-processed compositions can include the organo-disulfide in an amount of from about 0.002 to about 2 weight %, the silver sulfate in an amount of from about 0.025 to about 5 weight %, or the hindered amine light stabilizer in an amount of from about 1 to about 50 weight %.

Further, the melt-processed composition can comprise polypropylene, silver sulfate in an amount of from about 0.025 to about 5 weight %, a hindered amine light stabilizer in an amount of from about 1 to about 50 weight %, and an organo-disulfide in an amount of from about 0.002 to about 2 weight %.

The resulting melt-processed film, fiber, or article can have a b*IF value greater than 0.35 and a polyolefin that is polypropylene, silver sulfate in an amount of from about 0.025 to about 0.5 weight %, a hindered amine light stabilizer in an amount of from about 0.5 to about 5 weight %, and an organo-disulfide in an amount of from about 0.002 to about 0.5 weight %.

The resulting initial composition could be a masterbatch that can be further diluted in the compounder where the masterbatch is mixed with thermoplastic polymer.

The resulting composite could be a masterbatch that can be further diluted in a compounder where the masterbatch is mixed with thermoplastic polymer either simultaneously, same feeder, or sequentially, multiple feeders, resulting in a dilution of the masterbatch.

The basic procedures followed in producing the compositions of this invention or articles made from them comprise several different melt-processing methods. Several basic methods exist of incorporating additives (such as silver sulfate and the other composition components) within polymer articles on a large scale. One method is to dry blend a mixture of polyolefin, organo-disulfides, hindered amino light stabilizers, melt the dry mix together, followed by addition of silver sulfate; melt the dry mix together in an extruder to form a molten composition which is then pelletized; and melting and subsequently molding such pellets into a plastic article. Alternatively, one may mix conventional resin pellets and masterbatch concentrates containing the components and silver sulfate and molding in conventional molding equipment. The aforementioned molding steps may be performed preferably with injection molding equipment; however, other plastic-forming operations may also be utilized such as, and without limitation, blow molding, fiber extrusion, film formation, compression molding, and rotational molding. These alternative plastic article-forming operations would be well understood and appreciated by one of ordinary skill in this art.

Besides the polyolefin, silver sulfate, organo-disulfide, and hindered amine light stabilizers, the composition or composite material of the invention can include optional addenda. These addenda can include nucleating agents, antiblocking agents, basic co-stabilizers, blowing agents, fillers and reinforcing agents, plasticizers, light stabilizers and UV inhibitors, metal inhibitors, surfactants, intercalates, lactones, compatibilizers, coupling agents, impact modifiers, chain extenders, colorants, dyes (such as ultramarine blue and cobalt violet), pigments (such as titanium oxide, zinc oxide, talc, calcium carbonate), lubricants, emulsifiers, antistatic agents, dispersants such as fatty amides (such as stearamide), metallic salts of fatty acids (such as zinc stearate and magnesium stearate), processing aids, additional antioxidants, synergists, fluorescent whiteners, fire retardants, abrasives or roughening agents such as diatomaceous earth, cross linking agents, and foaming agents. These optional addenda and their corresponding amounts can be chosen according to need. Incorporation of these optional addenda in the purge material can be accomplished by any known method.

Melt-processed compositions and composites of this invention may be employed in a variety of applications. Typical uses include, but are not limited to, extruded and non-extruded face fibers for area rugs (rugs with polypropylene face fibers (such as commercial, retail or residential carpet), carpet backing (either primary or secondary backing), or the latex adhesive backings used in carpet (commercial, residential or retail), or area rugs (commercial or residential). In addition, melt-processed compositions of the invention may be used in liquid filtration media (such as non-woven filtration media for pools and spas, waste water treatment, potable water treatment, and industrial applications such as metalworking); non-woven air filtration media (such as commercial and residential furnace, HVAC or humidity control filters, air purifiers, and HEPA filters, and cabin air filters for automobiles and airplanes). Further, melt-processed compositions of the invention can be used for outdoor fabrics (such as woven and non-woven car and boat covers, tarps, tents, canvas, ducking, sails, ropes, pool covers, patio upholstery (such as umbrellas, awnings, seating), camping gear and geotextiles, building materials (such as drywall, weather stripping, insulation, housewrap and roof wrap), wall covering fabrics, flooring materials such as cement, concrete, mortar and tile, synthetic marble for kitchen and bath counters and sinks, sanitary ceramic composites, toilets, shower stalls and curtains, sealing materials (such as adhesives for plumbing and packaging, glazing for windows, tile and vitreous china, and grout), push buttons for elevators, handrails for stairs, mats, and knobs), industrial equipment (such as tape, tubing, barrier fabrics, conveyor belts, insulators and insulation for wire and cable, plumbing supplies and fixtures), gaskets, collection and storage equipment (including piping systems, silos, tanks and processing vessels) and coatings used on the inside of fire system sprinkler pipes), daily necessities (such as chopping boards, disposable gloves, bowls, kitchen drain baskets, kitchen refuse baskets, kitchen knife handles, chopsticks, tableware, table cloths, napkins, trays, containers, bags, lunch boxes, chopstick cases, dusters, sponges, brooms, mops, wipes, bathroom stools, washbowls, pales, cupboards, soap cases, shampoo holders, toothbrush holders, toothbrushes, razor blade handles, wrapping films, food wraps and packaging, canteens, emergency water tanks, toilet seats, hairbrushes, brush bristles, combs, scrubbers, tools and tool handles), cosmetics and cosmetic containers, and clothing. Other uses envisioned include incorporation of the compositions of the invention into stationary and writing materials (such as mechanical pencils, ball-point pens, pencils, erasers, floppy disk cases, clipboards, clear paper holders, fancy cases, video tape cases, photo-magnetic disk shells, compact disk cases, desk mats, binders, book covers, writing paper and pocket books), automobile parts (such as a steering wheels, armrests, panels, shift knobs, switches, keys, door knobs, assist grips, truck liners, convertible tops and interior liners), appliances (such as refrigerators, washing machines, vacuum cleaners and bags, air conditioners, clothing irons, humidifiers, dehumidifiers, water cleaners, dish washers and dryers, rice cookers, stationary and mobile telephones), copiers, touch panels for ATM or retail kiosks (such as photo-kiosks), textile products (such as socks, pantyhose, undergarments, inner liners for jackets, aprons, gloves and helmets, towels, bathing suits, toilet covers, cushion pads, curtains, carpet fibers, fiberfill for quilts and pillows, pillows, sheets, blankets, bedclothes, bedding, mattress ticking, sleeping bags, mattress cover pads and filling, pillow covers, nose and mouth masks, towels, caps, hats, and wigs), goods related to public transportation (such as overhead straps, handles and grips, levers, seats, seat belts, luggage and storage racks), sporting goods (such as balls, nets, pucks, whistles, mouth pieces, and racket handles), performance clothing, protective gear, helmets, indoor and outdoor artificial turf, shoe linings and reinforcements, tools, structures and ceremonial objects used in athletic events and the martial arts, medical applications (such as bandages, gauze, catheters, artificial limbs, implants, instruments, scrubs, facemasks, shields, reusable and disposable diapers, sanitary napkins, tampons, condoms, uniforms, gowns and other hospital garments requiring aggressive and harsh cleaning treatments to allow the garment to be safely worn by more than one person). Miscellaneous applications for the invention further involve inclusion in musical instruments (such as in reeds, strings, and mouthpieces), contact lens, lens keepers and holders, plastic credit/debit cards, sand-like materials for play boxes, jewelry and wrist watch bands.

Use of the compositions of this invention in polymer-wood composites is also contemplated. Over the past several years, a growing market has emerged for the use of polymer-wood composites to replace traditional solid wood products in end-use applications such as extruded and foam-filled extruded building and construction materials (such as window frames, exterior cladding, exterior siding, door frames, ducting, roof shingles and related roofline products, and exterior boardwalks and walkways); interiors and internal finishes (for example, interior paneling, decorative profiles, office furniture, kitchen cabinets, shelving, worktops, blinds and shutters, skirting boards, and interior railings); automotive (including door and head liners, ducting, interior panels, dashboards, rear shelves, trunk floors, and spare tire covers); garden and outdoor products (such as decking, fence posts and fencing, rails and railings, garden furniture, sheds and shelters, park benches, playground equipment, and playground surfaces); and finally, industrial applications (including industrial flooring, railings, marine pilings, marine bulkheads, fishing nets, railroad ties, pallets, etc.).

Another emerging application to which the present invention is particularly applicable is antimicrobial nonwoven fabrics. In general, continuous filament nonwoven fabric formation involves supplying a low viscosity molten polyolefin composition that is then extruded under pressure through a large number of micro-orifices in a plate known as a spinneret or die, which creates a plurality of continuous polymeric filaments. The filaments are then quenched and drawn, and collected to form a nonwoven web. Microfilaments may typically be on the order of about 20 µm in diameter, while super microfilaments may be on the order of 3-5 µm. Continuous filament nonwoven fabrics formed from super microfilaments are mainly used in air filters, as well as in artificial leathers and wipes. Commercial processes are well known in the art for producing continuous microfilament nonwoven fabrics of polyethylene and polypropylene. The present invention enables production of melt-processed polypropylene comprising silver sulfate that may then be incorporated into such fine filaments with greatly reduced change in coloration.

One method for making the composite is melt blending with the polyolefin using any suitable mixing device such as a single screw compounder, blender, paddle compounder such as a Brabender, spatula, press, extruder, or molder such as an injection molder. However, it is possible to use a suitable batch mixer, continuous mixer or twin-screw compounder such as a PolyLab or Leistritz, to ensure proper mixing. Twin-screw extruders are built on a building block principle. Thus, mixing of the silver sulfate, temperature, mixing rotations per minute (rpm), residence time of resin, as well as point of addition of the silver-based antimicrobial agent can be easily changed by changing screw design, barrel design and processing parameters. Similar machines are also provided by other twin-screw compounder manufacturers like Werner and Pfleiderrer, Berstorff, and the like, which can be operated either in the co-rotating or the counter-rotating mode.

One method for making the initial composition is to melt polyolefin in a glass, metal or other suitable vessel, followed by addition of the organo-disulfide. The polyolefin and other components (other than the silver sulfate) are mixed using a spatula until the additives are properly dispersed in the polyolefin, followed by the addition of silver sulfate. The silver sulfate is mixed using a spatula until it is appropriately dispersed in the polymer. Another method for making the composite is to melt the polyolefin in a small compounder, such as a Brabender compounder, followed by addition of the hindered amine light stabilizer and organo-disulfide until they are properly dispersed in the polyolefin, followed by addition of the silver sulfate until it is appropriately dispersed in the polyolefin. Yet in another method such as in the case of a twin-screw compounder, this compounder is provided with main feeders through which polyolefin pellets or powders are fed. The additives can be mixed with and fed simultaneously with the polyolefin pellets or powders. The additives can also be fed using a feeder located downline from the polyolefin feeder. Both procedures will produce an initial composition. The silver sulfate is then fed using a top feeder or using a side stuffer. If the side stuffer is used to feed the silver sulfate then the feeder screw design needs to be appropriately configured. The preferred mode of addition of the silver sulfate to the thermoplastic polyolefin composite is by the use of a side stuffer, although a top feeder can be used, to ensure proper viscous mixing and to ensure dispersion of the silver sulfate through the initial composition polyolefin matrix as well as to control the thermal history.

Alternatively, the initial composition containing the hindered amine light stabilizer and organo-disulfide can be compounded and collected, then fed through the main feeder before addition of the silver sulfate. The resulting composite material obtained after compounding can be further processed into pellets, granules, strands, ribbons, fibers, powder, films, plaques, foams and the like for subsequent use.

Thus, in some embodiments, the following are compounded, in order:

the polyolefin with the hindered amine light stabilizer (such as a polymeric HALS), then the organo-disulfide, and then silver sulfate.

In still other embodiments, the melt-processing method of this invention prepares a polyolefin composition having a $b*IF$ value greater than zero and comprises the following component concentrations:

the silver sulfate is present in an amount of from about 0.025 to about 5 weight %, the hindered amine light stabilizer is present in an amount of from about 1 to about 50 weight %, and the organo-disulfide is present in an amount of from about 0.002 to about 2 weight %.

The following examples are intended to demonstrate, but not to limit, the invention.

EXAMPLES

The change in color of a melt-processed polymer composite due to exposure to light was quantified by first pressing aliquots of the melt-processed polymer composite into two flat plaques. One of the plaques was stored in a black bag and kept in a dark container unexposed to any light, defined as dark. The other plaque was exposed on one side for one week to an unfiltered cool-white fluorescent light, then turned and exposed on the other side for one week to an unfiltered cool-white fluorescent light, this sample defined as light. The distance between the exposed plaque and the cool-white fluorescent light source was 152.4 cm. The two plaques for each polymer composite, both dark and light, were then measured for spectral response in a HunterLab UltraScan XE calorimeter. Color is reported in terms of the 1976 $b*$ coordinates, where $b*$ is a measure of the yellowness (an increase in $b*$ value indicates increased yellowness) or blueness (a decrease in $b*$ value indicates increased blueness) of the plaque. A further description of the calorimetric test procedure is contained in Billmeyer, F. W., et al., *Principles of Color Technology*, 2$^{nd}$ Edition, pp. 62-64, published by John Wiley & Sons, Inc., 1981; or in ASTM Designations: D 2244-05 and D 1729-96.

A b* Improvement Factor (b*IF) was used to determine if a melt-processed composite comprised of polyolefin, HALS, a silver containing antimicrobial, and an additive (composition defined as additive) demonstrated improved color stability (less change in yellow or blue coloration) after exposure to light when compared to the melt-processed composite not containing the additive (composition defined as check). The value of b*IF is defined as:

$$b*IF = \frac{(|b*dark_{check} - b*light_{check}| - |b*dark_{additive} - b*light_{additive}|)}{|b*dark_{check} - b*light_{check}|}$$

wherein:

$b*dark_{check}$ is the measured b* value for a check plaque containing polyolefin, HALS, and silver containing antimicrobial that has been kept dark $b*light_{check}$ is the measured b* value for a check plaque containing polyolefin, HALS, and silver containing antimicrobial that has been exposed to light $b*dark_{additive}$ is the measured b* value for a check plaque containing polyolefin, HALS, silver containing antimicrobial, and additive that has been kept dark $b*light_{additive}$ is the measured b* value for a check plaque containing polyolefin, HALS, silver containing antimicrobial, and additive that has been exposed to light $|b*dark_{check} - b*light_{check}|$ is the absolute value of $b*dark_{check} - b*light_{check}$ $|b*dark_{additive} - b*light_{additive}|$ is the absolute value of $b*dark_{additive} - b*light_{additive}$ A b*IF value greater than zero is an indication that the use of an additive in a melt-processed composition has been shown to improve light stability by reducing the yellowing or bluing when compared to the corresponding check melt-processed composite not containing the additive. A positive b*IF value represents the relative improvement in light stability for an inventive additive. A b*IF value greater than [0.35] is preferred. A b*IF value equal to zero is an indication that the use of an additive in a melt-processed composition has been shown to have no effect on the light induced yellowing or bluing, and the composition is not inventive. By default, a check sample compared to itself will give a b*IF value of zero. A b*IF value less than zero is an indication that the use of an additive in a melt-processed composition has been shown to have an increase in light induced yellowing or bluing, and the additive composition is not inventive.

The chemicals used in the following examples are as follows:

| Component | Chemical Name | CAS No. | Supplier | Identifier |
|---|---|---|---|---|
| PP 3155 | Polypropylene | 9003-07-0 | ExxonMobile | PP |
| PE811A | Polyethylene | 9002-88-4 | Westlake Chemical | PE |
| HA88 FD Hindered amine light stabilizer HALS | 1,3-Propanediamine, N,N''-1,2-ethanediylbis-,polymer with 2,4,6-trichloro-1,3,5-triazine, reaction products with N-butyl-2,2,6,6-tetramethyl-4-piperidinamine | 136504-96-6 | 3V | HA88 |
| Chimassorb 944 Hindered amine light stabilizer HALS | Poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]] | 71878-19-8 | Ciba | C944 |
| Chimassorb 2020 Hindered amine light stabilizer HALS | 1,6-Hexanediamine, N1,N6-bis(2,2,6,6-tetramethyl-4-piperidinyl)-, polymer with 2,4,6-trichloro-1,3,5 triazine, reaction products with, N-butyl-1-butanamine and N-butyl-2,2,6,6-tetramethyl-4-piperidinamine | 192268-64-7 | Ciba | C2020 |
| Hostanox SE 10 Secondary Antioxidant Organo-Disulfide | Dioctadecyl disulfide | 2500-88-1 | Clariant | SE10 |
| Diphenyl Disulfide Secondary Antioxidant Organo-Disulfide | Diphenyl disulphide | 882-33-7 | Eastman Kodak | DPDS |
| Hostanox PAR 62 Secondary Antioxidant Organo-Phosphite | Bis(2,4-di-tert-butylphenyl) pentaerythritol diphosphite | 26741-53-7 | Clariant | PAR62 |
| Irgafos 168 | Phenol, 2,4-bis(1,1- | 31570-04-4 | CIBA | IRG168 |

| Component | Chemical Name | CAS No. | Supplier | Identifier |
|---|---|---|---|---|
| Secondary Antioxidant Organo-Phosphite | dimethylethyl)-, 1,1',1"-phosphite | | | |
| Hostanox X O10 Primary Antioxidant Organo-Phenol | Pentaerythrityl-tetrakis 3-(3,5-di-tert-butyl-4-hydroxy-phenyl)propionate | 6683-19-8 | Clariant | O10 |
| $Ag_2SO_4$ Antimicrobial Agent | Silver sulfate | 10294-26-5 | Cascade Chemicals | XC |
| AgCl Antimicrobial Agent | Silver Chloride | 7783-90-6 | Eastman Kodak | XA |
| Ag Antimicrobial Agent | Silver | 7440-22-4 | Eastman Kodak | XG |

The following Examples demonstrate the use of an organo-disulfide additive in a melt-processed composite comprised of polypropylene, C2020, and XC source of the silver-based antimicrobial agent.

Control 1: PP C2020 XC Check

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a powder comprised of 10 grams C2020, was added to the feed chamber and compounded 2.5 minutes under a dry nitrogen purge. Following the compounding of the PP and C2020 powder, 1 gram of XC was added to the feed chamber and the final composite was compounded 3.5 minutes under a nitrogen purge. The mixing paddles were stopped, and the feed chamber was dismantled. The C2020 check final composite sample was removed from the chamber walls and paddles, and two aliquots were pressed into plaques onto a stainless steel plate, with the original stainless steel plate temperature at 23° C. One resulting plaque was kept dark, one resulting plaque was exposed to unfiltered cool-white fluorescent light as described previously. Both plaques were measured for color using a HunterLab UltraScan XE calorimeter, with b* values recorded and presented in TABLE I below.

Invention Example 1

PP C2020 XC Additive

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a premixed powder comprised of 10 grams C2020 and 0.04 grams SE10, was added to the feed chamber and compounded 2.5 minutes under a dry nitrogen purge. Following the compounding of the PP and premixed powder, 1 gram of XC was added to the feed chamber and the final composite was compounded 3.5 minutes under a nitrogen purge. The mixing paddles were stopped, and the feed chamber was dismantled. The C2020 additive final composite sample was removed from the chamber walls and paddles, and two aliquots were pressed into plaques onto a stainless steel plate, with the original stainless steel plate temperature at 23° C. One resulting plaque was kept dark, and one resulting plaque was exposed to unfiltered cool-white fluorescent light as described previously. Both plaques were measured for color using a HunterLab UltraScan XE calorimeter, with b* values recorded and presented in TABLE I below.

TABLE I below contains calorimetric results wherein the b*IF result for Invention Example 1 is referenced to the Control 1 containing no-additive.

TABLE I

| Example | b*dark | b*light | $|b^*dark_{check} - b^*light_{check}|$ | $|b^*dark_{additive} - b^*light_{additive}|$ | b*IF |
|---|---|---|---|---|---|
| Control 1 | 9.94 | −5.27 | 15.21 | — | — |
| Invention 1 | 7.44 | 3.94 | — | 3.50 | 0.77 |

The b*IF results in TABLE I indicate that the Invention Example 1 melt-processed composite comprised of PP, C2020 HALS, XC $Ag_2SO_4$ and SE10 organo-disulfide provides an advantage of reduced coloration change. The b*IF result greater than zero demonstrates that the addition of an organo-disulfide additive is effective in reducing the amount of change in b* discoloration, due to exposure to light, when compared to the Control 1 melt-processed composite that contained no organo-disulfide additive.

The following Examples demonstrate the use of an organo-disulfide additive in a melt-processed composite comprised of PP, C944 and XC source of the silver-based antimicrobial agent.

Control 2: PP C944 XC Check

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a powder comprised of 10 grams C944, was added to the feed chamber and compounded 2.5 minutes under a dry nitrogen purge. Following the compounding of the PP and C944 powder, 1 gram of XC was added to the feed chamber and the final composite was compounded 3.5 minutes under a nitrogen purge. The mixing paddles were stopped, and the feed chamber was dismantled. The C944 check final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented in TABLE II below.

Invention Example 2

PP C944 XC Additive

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a premixed powder comprised of 10 grams C944 and 0.04 grams SE10, was added to the feed chamber and compounded 2.5 minutes under a dry nitrogen purge. Following the compounding of the PP and premixed powder, 1 gram of XC was added to the feed chamber and the final composite was compounded 3.5 minutes under a nitrogen purge. The mixing paddles were stopped, and the feed chamber was dismantled. The C944 additive final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented in TABLE II below that contains calorimetric results for both Examples wherein the b*IF result for Invention Example 2 is referenced to Control 2.

TABLE II

| Example | B*dark | b*light | \|b*dark$_{check}$ − b*light$_{check}$\| | \|b*dark$_{additive}$ − b*light$_{additive}$\| | b*IF |
|---|---|---|---|---|---|
| Control 2 | 12.43 | 4.16 | 8.27 | — | — |
| Invention 2 | 12.6 | 7.50 | — | 5.10 | 0.38 |

The b*IF results in TABLE II indicate that the Invention Example 2 melt-processed composite comprised of PP, C944 HALS, XC Ag$_2$SO$_4$ and SE10 organo-disulfide provided an improvement. The b*IF result greater than zero demonstrates that the addition of an organo-disulfide additive is effective in reducing the amount of change in b* discoloration, due to exposure to light, when compared to the Control 2 melt-processed composite that contained no organo-disulfide additive.

The following Examples demonstrate the advantage from use of an organo-disulfide additive in a melt-processed composite comprised of PP, HA88 and XC source of the silver-based antimicrobial agent.

Control 3: PP HA88 XC Check

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a powder comprised of 10 grams HA88, was added to the feed chamber and compounded 2.5 minutes under a dry nitrogen purge. Following the compounding of the PP and HA88 powder, 1 gram of XC was added to the feed chamber and the final composite was compounded 3.5 minutes under a nitrogen purge. The mixing paddles were stopped, and the feed chamber was dismantled. The HA88 check final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE IV.

Invention Examples 3-9

PP HA88 XC Additive

In the following TABLE III shows the compositions of these Invention Examples.

TABLE III

| | | Premix Powder | | | |
|---|---|---|---|---|---|
| Example | Polymer | HALS | Additive | Ag$_2$SO$_4$ | |
| Invention 3 | 29 grams PP | 10 grams HA88 | 0.08 grams SE10 | 1 gram XC | |
| Invention 4 | 29 grams PP | 10 grams HA88 | 0.04 grams SE10 | 1 gram XC | |
| Invention 5 | 29 grams PP | 10 grams HA88 | 0.02 grams SE10 | 1 gram XC | |
| Invention 6 | 29 grams PP | 10 grams HA88 | 0.04 grams O10 0.04 grams SE10 | 1 gram XC | |
| Invention 7 | 29 grams PP | 10 grams HA88 | 0.04 grams DPDS | 1 gram XC | |
| Invention 8 | 29 grams PP | 10 grams HA88 | 0.02 grams DPDS | 1 gram XC | |
| Invention 9 | 29 grams PP | 10 grams HA88 | 0.004 grams DPDS | 1 gram XC | |

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a premixed powder comprised of 10 grams HA88 and an additive, was added to the feed chamber and compounded 2.5 minutes under a dry nitrogen purge. Following the compounding of the PP and premixed powder, 1 gram of XC was added to the feed chamber and the final composite was compounded 3.5 minutes under a nitrogen purge. The mixing paddles were stopped, and the feed chamber was dismantled. The HA88 additive final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE IV where the b*IF results are referenced to the Control 3 composite.

TABLE IV

| Example | B*dark | B*light | \|b*dark$_{check}$ − b*light$_{check}$\| | \|b*dark$_{additive}$ − b*light$_{additive}$\| | b*IF |
|---|---|---|---|---|---|
| Control 3 | 20.26 | 8.83 | 11.43 | — | — |
| Invention 3 | 4.84 | 4.29 | — | 0.55 | 0.95 |
| Invention 4 | 10.38 | 7.63 | — | 2.75 | 0.76 |
| Invention 5 | 14.04 | 7.08 | — | 6.96 | 0.39 |
| Invention 6 | 10.75 | 6.32 | — | 4.43 | 0.61 |
| Invention 7 | 4.98 | 5.73 | — | 0.75 | 0.93 |
| Invention 8 | 2.46 | 2.78 | — | 0.32 | 0.97 |
| Invention 9 | 5.11 | 2.88 | — | 2.23 | 0.80 |

The b*IF results in TABLE IV indicate that the Invention Examples 3-6 melt-processed composites comprised of PP, HA88 HALS, XC Ag$_2$SO$_4$ and SE10 organo-disulfide and Invention Examples 7-9 melt-processed composites comprised of PP, HA88 HALS, XC Ag$_2$SO$_4$ and DPDS organo-disulfide provided improvements. The b*IF results greater than zero demonstrate that the addition of an organo-disulfide additive is effective in reducing the amount of change in b* discoloration, due to exposure to light, when compared to the Control 3 melt-processed composite that contained no organo-disulfide additive. Invention Example 6 containing the combined additives of an organo-phenol (O10) and an organo-disulfide (SE10) in the presence of PP, HALS, and Ag$_2$SO$_4$ did not offer any significant advantage over Invention Example 4 containing only the organo-disulfide (SE10) additive.

Comparative Examples 1-3

These Comparative Examples demonstrate that the use of nonorgano-disulfide additives (outside the scope of this invention) in a melt-processed composite comprised of PP, HA88 and XC source of the silver-based antimicrobial agent. The results were compared to the Control 3 composite for determination of b*IF values. The compositions are shown in the following TABLE V.

TABLE V

| Example | Polymer | HALS | Premix Powder Additive | Ag$_2$SO$_4$ |
|---|---|---|---|---|
| Comparative 1 | 29 grams PP | 10 grams HA88 | 0.04 grams IRG168 | 1 gram XC |
| Comparative 2 | 29 grams PP | 10 grams HA88 | 0.04 grams PAR62 | 1 gram XC |
| Comparative 3 | 29 grams PP | 10 grams HA88 | 0.04 grams O10 | 1 gram XC |

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a premixed powder comprised of 10 grams HA88 and an additive, was added to the feed chamber and compounded 2.5 minutes under a dry nitrogen purge. Following the compounding of the PP and premixed powder, 1 gram of XC was added to the feed chamber and the final composite was compounded 3.5 minutes under a nitrogen purge. The mixing paddles were stopped, and the feed chamber was dismantled. The HA88 additive final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE VI wherein the b*IF results were referenced to the Control 3 composite.

TABLE VI

| Example | b*dark | b*light | |b*dark$_{check}$ − b*light$_{check}$| | |b*dark$_{additive}$ − b*light$_{additive}$| | b*IF |
|---|---|---|---|---|---|
| Control 3 | 20.26 | 8.83 | 11.43 | — | — |
| Comparative 1 | 20.98 | 8.71 | — | 12.27 | −0.07 |
| Comparative 2 | 19.67 | 6.28 | — | 13.39 | −0.17 |
| Comparative 3 | 20.27 | 6.81 | — | 13.46 | −0.18 |

The b*IF results in TABLE VI indicate that Comparative Examples 1-3 melt-processed composites comprised of PP, HA88 HALS, XC Ag$_2$SO$_4$ and nonorgano-disulfide additives do not provide improvements. The b*IF results of less than zero demonstrate that the addition of a nonorgano-disulfide additive is not effective in reducing the amount of change in b* discoloration, due to exposure to light, when compared to the Control 3 melt-processed composite that contained no organo-disulfide additive. The additives used in Comparative Examples 1-2 were organo-phosphites and the additive used in Comparative Example 3 was an organo-phenol. Organo-phosphites and organo-phenols are commonly used in melt processing of polyolefins and the results of TABLE VI indicate that it is not predictable as to which additives can be used in the melt processing of polyolefins containing silver sulfate to effectively reduce reducing b* discoloration, due to exposure to light.

The following Control 4 and Invention Example 10 relate to melt-processed composites comprised of polyethylene, HA88 and XC as the silver-based antimicrobial agent.

Control 4: PE HA88 XC Check

A Brabender paddle compounder was preheated to 220° C. and the mixing paddles were set to 60 rpm. Into the feed chamber was charged 29 grams of PE and compounded 1 minute under a dry nitrogen purge. Following the melting of the PE, a powder comprised of 10 grams HA88, was added to the feed chamber and compounded 2.5 minutes under a dry nitrogen purge. Following the compounding of the PE and HA88 powder, 1 gram of XC was added to the feed chamber and the final composite was compounded 3.5 minutes under a nitrogen purge. The mixing paddles were stopped, and the feed chamber was dismantled. The HA88 check final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE VII.

Invention Example 10

PE HA88 XC Additive

A Brabender paddle compounder was preheated to 220° C. and the mixing paddles were set to 60 rpm. Into the feed chamber was charged 29 grams of PE and compounded 1 minute under a dry nitrogen purge. Following the melting of the PE, a premixed powder comprised of 10 grams HA88 and 0.04 grams SE10, was added to the feed chamber and compounded 2.5 minutes under a dry nitrogen purge. Following the compounding of the PE and premixed powder, 1 gram of XC was added to the feed chamber and the final composite was compounded 3.5 minutes under a nitrogen purge. The mixing paddles were stopped, and the feed chamber was dismantled. The HA88 additive final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE VII wherein the b*IF results for Invention Example 10 are referenced to the Control 4 composite.

TABLE VII

| Example | B*dark | b*light | \|b*dark$_{check}$ − b*light$_{check}$\| | \|b*dark$_{additive}$ − b*light$_{additive}$\| | b*IF |
|---|---|---|---|---|---|
| Control 4 | 16.59 | 13.01 | 3.58 | — | — |
| Invention 10 | 4.53 | 5.35 | — | 0.82 | 0.77 |

The b*IF results in TABLE VII indicate that the Invention Example 10 melt-processed composite comprised of PE, HA88 HALS, XC $Ag_2SO_4$ and SE10 organo-disulfide provided improvement because the b*IF result was greater than zero, demonstrating that the addition of an organo-disulfide additive was effective in reducing the amount of change in b* discoloration, due to exposure to light, when compared to the Control 4 melt-processed composite that contained no organo-disulfide additive.

The following Comparative Example 4 and Control 5 were melt-processed composites containing PP, HA88 and XA source of the silver-based antimicrobial agent.

Control 5: PP HA88 XA Check

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a powder comprised of 10 grams HA88, was added to the feed chamber and compounded 2.5 minutes under a dry nitrogen purge. Following the compounding of the PP and HA88 powder, 1 gram of XA was added to the feed chamber and the final composite was compounded 3.5 minutes under a nitrogen purge. The mixing paddles were stopped, and the feed chamber was dismantled. The HA88 check final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE VIII.

Comparative Example 4

PP HA88 XA Additive

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a premixed powder comprised of 10 grams HA88 and 0.04 grams SE10, was added to the feed chamber and compounded 2.5 minutes under a dry nitrogen purge. Following the compounding of the PP and premixed powder, 1 gram of XA was added to the feed chamber and the final composite was compounded 3.5 minutes under a nitrogen purge. The mixing paddles were stopped, and the feed chamber was dismantled. The HA88 additive final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE VIII wherein the b*IF results for Comparative Example 4 are referenced to the Control 5 composite.

TABLE VIII

| Example | b*dark | b*light | \|b*dark$_{check}$ − b*light$_{check}$\| | \|b*dark$_{additive}$ − b*light$_{additive}$\| | b*IF |
|---|---|---|---|---|---|
| Control 5 | 10.13 | 8.49 | 1.64 | — | — |
| Comparative 4 | 9.22 | 6.29 | — | 2.93 | −0.44 |

The b*IF results in TABLE VIII indicate that Comparative Example 4 melt-processed composite comprised of PP, HA88 HALS, XA AgCl and SE10 organo-disulfide did not provide an improvement. The b*IF result less than zero demonstrates that the addition of an organo-disulfide additive in a composite that contains AgCl as the antimicrobial agent, is not effective in reducing the amount of change in b* discoloration, due to exposure to light, when compared to the corresponding Control 5 melt-processed composite that contained no organo-disulfide additive. The results of TABLE VIII 8 indicate that it is not obvious that using an organo-disulfide additive will be effective in reducing b* discoloration, due to exposure to light, for melt-processed composites containing PP, HALS, and specific silver containing antimicrobial agents such as silver sulfate.

The following Comparative Example 5 and Control 6 demonstrate the use of an organo-disulfide additive in a melt processed composite comprised of polypropylene, HA88 and XG as the silver-based antimicrobial agent.

Control 6: PP HA88 XG Check

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a powder comprised of 10 grams HA88, was added to the feed chamber and compounded 2.5 minutes under a dry nitrogen purge. Following the compounding of the PP and HA88 powder, 1 gram of silver powder XG was added to the feed chamber and the final composite was compounded 3.5 minutes under a nitrogen purge. The mixing paddles were stopped, and the feed chamber was dismantled. The HA88 check final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE IX.

Comparative Example 5

PP HA88 XG Additive

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a premixed powder comprised of 10 grams HA88 and 0.04 grams SE10, was added to the feed chamber and compounded 2.5 minutes under a dry nitrogen purge. Following the compounding of the PP and premixed powder, 1 gram of silver powder XG was added to the feed chamber and the final composite was compounded 3.5 minutes under a nitrogen purge. The mixing paddles were stopped, and the feed chamber was dismantled. The HA88 additive final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE IX wherein the b*IF results for Comparative 5 are referenced to the Control 6 results.

TABLE IX

| Example | b*dark | b*light | \|b*dark$_{check}$ − b*light$_{check}$\| | \|b*dark$_{additive}$ − b*light$_{additive}$\| | b*IF |
|---|---|---|---|---|---|
| Control 6 | 11.09 | 9.23 | 1.86 | — | — |
| Comparative 5 | 7.92 | 5.37 | — | 2.55 | −0.37 |

The b*IF results in TABLE IX indicate that Comparative Example 5 melt processed composite comprised of PP, HA88 HALS, silver powder XG and SE10 organo-disulfide did not show improvement. The b*IF result less than zero demonstrates that the addition of an organo-disulfide additive in a composite that contains silver powder as the antimicrobial agent, is not effective in reducing the amount of change in b* discoloration, due to exposure to light, when compared to the Control 6 melt processed composite that contained no organo-disulfide additive. These results indicate that it is not obvious that using an organo-disulfide additive will be effective in reducing b* discoloration, due to exposure to light, for melt processed composites containing PP, HALS, and silver sulfate.

The Invention Examples 11 and 12 demonstrate organo-disulfide additive in a melt processed composite comprised of polypropylene, HA88 and XC source of the silver-based antimicrobial agent. They were compared to Control 3 and Invention Example 4 to show the various methods of addition of the organo-disulfide.

Invention Example 11

PP HA88 XC Additive

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a powder comprised of 10 grams HA88 was added to the feed chamber and compounded 2.5 minutes under a dry nitrogen purge. Following the compounding of the PP and HA88 powder, a premixed powder comprised of 1 gram of XC and 0.04 grams of SE10 was added to the feed chamber and the final composite was compounded 3.5 minutes under a nitrogen purge. The mixing paddles were stopped, and the feed chamber was dismantled. The HA88 additive final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE X.

Invention Example 12

PP HA88 XC Additive

A Brabender paddle compounder was preheated to 220° C. and the mixing paddles were set to 60 rpm. Into the feed chamber was charged 29 grams of PP and compounded 1 minute under a dry nitrogen purge. Following the melting of the PP, a powder comprised of 10 grams HA88 was added to the feed chamber and compounded 2.5 minutes under a dry nitrogen purge. Following the compounding of the PP and HA88 powder, 1 gram of XC was added to the feed chamber and compounded 1.5 minutes under a dry nitrogen purge. Following the compounding of the PP, HA88 powder, and XC powder, 0.04 grams of SE10 was added to the feed chamber and the final composite was compounded 2 minutes under a nitrogen purge. The mixing paddles were stopped, and the feed chamber was dismantled. The HA88 additive final composite sample was removed from the chamber walls and paddles, and two aliquots were pressed into plaques onto a stainless steel plate, with the original stainless steel plate temperature at 23° C. One resulting plaque was kept dark and one resulting plaque was exposed to unfiltered cool-white fluorescent light as described previously. Both plaques were measured for color using a HunterLab UltraScan XE calorimeter, with b* values recorded and presented below in TABLE X wherein the b*IF results for Invention Examples 4, 11, and 12 are referenced to the Control 3 composite.

TABLE X

| Example | b*dark | b*light | \|b*dark$_{check}$ − b*light$_{check}$\| | \|b*dark$_{additive}$ − b*light$_{additive}$\| | b*IF |
|---|---|---|---|---|---|
| Control 3 | 20.26 | 8.83 | 11.43 | — | — |
| Invention 4 | 10.38 | 7.63 | | 2.75 | 0.76 |
| Invention 11 | 9.11 | 7.60 | | 1.51 | 0.87 |
| Invention 12 | 9.91 | 5.29 | | 4.62 | 0.60 |

The b*IF results in TABLE X indicate that Examples 4, 11, and 12 melt processed composites comprised of PP, HA88 HALS, XC Ag$_2$SO$_4$ and SE10 organo-disulfide provide improvements. The b*IF results greater than zero demonstrate that the addition of an organo-disulfide additive in a composite that contains $Ag_2SO_4$ as the antimicrobial agent is effective in reducing the amount of change in b* discoloration, due to exposure to light, when compared to the Control 3 that contains no organo-disulfide additive. The results of TABLE X also indicate that the method of addition of the organo-disulfide before (Invention Example 4), during (Invention Example 11), or after (Invention Example 12) the addition of $Ag_2SO_4$ will produce a melt processed composite that has a positive b*IF value after the composite has been exposed to light. The results of TABLE X 10 also demonstrate that the method of adding the organo-disulfide before or during $Ag_2SO_4$ addition will result in a more positive b*IF value, making these methods of organo-disulfide addition more advantageous.

The invention has been described in detail with particular reference to certain preferred embodiments thereof, but it will be understood that variations and modifications can be effected within the spirit and scope of the invention.

The invention claimed is:

1. A melt-processed composition comprising a polyolefin having dispersed therein at least 0.01 weight % of silver sulfate, at least 0.5 weight % of a hindered amine light stabilizer, and at least 0.001 weight % of an organo-disulfide.

2. The melt-processed composition of claim 1 having a b*IF value greater than zero.

3. The melt-processed composition of claim 1 having a b*IF value greater than or equal to 0.35.

4. The melt-processed composition of claim 1 wherein said organo-disulfide is present in an amount of from about 0.002 to about 2 weight %.

5. The melt-processed composition of claim 1 wherein said silver sulfate is present in an amount of from about 0.025 to about 5 weight %.

6. The melt-processed composition of claim 1 wherein said hindered amine light stabilizer is present in an amount of from about 1 to about 50 weight %.

7. The melt-processed composition of claim 1 wherein said hindered amine light stabilizer is a polymeric sterically hindered amine light stabilizer.

8. The melt-processed composition of claim 7 wherein said polymeric hindered amine light stabilizer is selected from the group consisting of:
   a) 1,3-propanediamine,N,N"-1,2-ethanediylbis-, polymer with 2,4,6-trichloro-1,3,5-triazine, reaction products with N-butyl-2,2,6,6-tetramethyl-4-piperidinamine,
   b) poly[[6-[(1,1,3,3-tetramethylbutyl)amino]-1,3,5-triazine-2,4-diyl][(2,2,6,6-tetramethyl-4-piperidinyl) imino]-1,6-hexanediyl[(2,2,6,6-tetramethyl-4-piperidinyl)imino]], and
   c) 1,6-hexanediamine, N1,N6-bis(2,2,6,6-tetramethyl-4-piperidinyl)-, polymer with 2,4,6-trichloro-1,3,5 triazine, reaction products with, N-butyl-1-butanamine and N-butyl-2,2,6,6-tetramethyl-4-piperidinamine; and
   said organo-disulfide is octadecyl disulfide or diphenyl disulfide.

9. The melt-processed composition of claim 1 wherein said polyolefin is polypropylene, said silver sulfate is present in an amount of from about 0.025 to about 5 weight %, said hindered amine light stabilizer is present in an amount of from about 1 to about 50 weight %, and said organo-disulfide is present in an amount of from about 0.002 to about 2 weight %.

10. The melt-processed composition of claim 1 that is a masterbatch composition comprising at least 0.1 weight % silver sulfate, at least 5 weight % of a hindered amine light stabilizer, and at least 0.01% of an organo-disulfide, and that has a b*IF value greater than zero.

11. The melt-processed composition of claim 10 wherein said hindered amine light stabilizer is a polymeric sterically hindered amine light stabilizer.

12. The melt-processed composition of claim 10 wherein said polymeric hindered amine light stabilizer is selected from the group consisting of:
   a) 1,3-propanediamine,N,N"-1,2-ethanediylbis-, polymer with 2,4,6-trichloro-1,3,5-triazine, reaction products with N-butyl-2,2,6,6-tetramethyl-4-piperidinamine,
   b) poly[[6-[(1,1,3,3-tetramethylbutyl)amino]-1,3,5-triazine-2,4-diyl][(2,2,6,6-tetramethyl-4-piperidinyl) imino]-1,6-hexanediyl[(2,2,6,6-tetramethyl-4-piperidinyl)imino]], and
   c) 1,6-hexanediamine,N1,N6-bis(2,2,6,6-tetramethyl-4-piperidinyl)-, polymer with 2,4,6-trichloro-1,3,5 triazine, reaction products with, N-butyl-1-butanamine and N-butyl-2,2,6,6-tetramethyl-4-piperidinamine, and
   said organo-disulfide is octadecyl disulfide or diphenyl disulfide.

13. A melt-processed film, fiber, or article comprising a polyolefin having dispersed therein at least 0.01 weight % of silver sulfate, at least 0.1 weight % of a hindered amine light stabilizer, and at least 0.001 weight % of an organo-disulfide.

14. The melt-processed film, fiber, or article of claim 13 wherein said organo-disulfide is present in an amount of from about 0.002 to about 0.5 weight %.

15. The melt-processed film, fiber, or article of claim 13 wherein said silver sulfate is present in an amount of from about 0.025 to about 0.5 weight %.

16. The melt-processed film, fiber, or article of claim 13 wherein said hindered amine light stabilizer is present in an amount of from about 0.5 to about 5 weight %, and that is a polymeric sterically hindered amine light stabilizer.

17. The melt-processed film, fiber, or article of claim 13 wherein said polymeric hindered amine light stabilizer is selected from the group consisting of:
   a) 1,3-propanediamine,N,N"-1,2-ethanediylbis-, polymer with 2,4,6-trichloro-1,3,5-triazine, reaction products with N-butyl-2,2,6,6-tetramethyl-4-piperidinamine,
   b) poly[[6-[(1,1,3,3-tetramethylbutyl)amino]-1,3,5-triazine-2,4-diyl][(2,2,6,6-tetramethyl-4-piperidinyl) imino]-1,6-hexanediyl[(2,2,6,6-tetramethyl-4-piperidinyl)imino]], and
   c) 1,6-hexanediamine,N1,N6-bis(2,2,6,6-tetramethyl-4-piperidinyl)-, polymer with 2,4,6-trichloro-1,3,5 triazine, reaction products with, N-butyl-1-butanamine and N-butyl-2,2,6,6-tetramethyl-4-piperidinamine, and
   said organo-disulfide is octadecyl disulfide or diphenyl disulfide.

18. The melt-processed film, fiber, or article of claim 13 having a b*IF value greater than 0.35 and wherein said polyolefin is polypropylene, said silver sulfate is present in an amount of from about 0.025 to about 0.5 weight %, said hindered amine light stabilizer is present in an amount of from about 0.5 to about 5 weight %, and said organo-disulfide is present in an amount of from about 0.002 to about 0.5 weight %.

19. A melt-processing method of preparing a polyolefin composition with antimicrobial properties, comprising:
   A) blending a polyolefin, hindered amine light stabilizer, and organo-disulfide, in any order, to provide a polyolefin composite, and
   B) subsequently, adding silver sulfate to said polyolefin composite.

20. The melt-processing method of claim 19 wherein the following are compounded, in order:

said polyolefin with said hindered amine light stabilizer, then said organo-disulfide, and then silver sulfate.

21. The melt-processing method of claim 19 wherein the prepared polyolefin composition has a b*IF value greater than zero and comprises the following component concentrations:
said silver sulfate is present in an amount of from about 0.025 to about 5 weight %, said hindered amine light stabilizer is present in an amount of from about 1 to about 50 weight %, and said organo-disulfide is present in an amount of from about 0.002 to about 2 weight %.

22. A process of forming a polymer composite comprising a polyolefin, a hindered amine light stabilizer, an organo-disulfide additive, and silver sulfate, wherein the composite has a b*IF value greater than zero, wherein the process comprises:
heating said polyolefin at least to melting point;
obtaining said hindered amine light stabilizer,
obtaining said silver sulfate antimicrobial agent;
obtaining said organo-disulfide additive; and
carrying out one of the following options a) through c) to form said polymer composite:
a) compounding the heated polyolefin with said hindered amine light stabilizer and said organo-disulfide additive, then adding said silver sulfate antimicrobial agent,
b) mixing said silver sulfate antimicrobial with said organo-disulfide additive, then compounding the resulting mixture with the heated polyolefin and said hindered amine light stabilizer, and
c) compounding the heated polyolefin and hindered amine light stabilizer with said silver sulfate antimicrobial agent, then adding said organo-disulfide additive.

* * * * *